United States Patent
Weber et al.

(10) Patent No.: US 12,323,712 B2
(45) Date of Patent: Jun. 3, 2025

(54) IMAGE EXPOSURE TECHNIQUES FOR OPHTHALMIC MICROSCOPE DEVICES

(71) Applicant: Haag-Streit AG, Köniz (CH)

(72) Inventors: Alain Weber, Köniz (CH); Philipp Gloor, Köniz (CH)

(73) Assignee: Haag-Streit AG, Köniz (CH)

( * ) Notice: Subject to any disclaimer, the term of this patent is extended or adjusted under 35 U.S.C. 154(b) by 163 days.

(21) Appl. No.: 18/265,851

(22) PCT Filed: Jan. 22, 2021

(86) PCT No.: PCT/EP2021/051481
§ 371 (c)(1),
(2) Date: Jun. 7, 2023

(87) PCT Pub. No.: WO2022/156904
PCT Pub. Date: Jul. 28, 2022

(65) Prior Publication Data
US 2023/0379589 A1    Nov. 23, 2023

(51) Int. Cl.
*A61F 9/007* (2006.01)
*A61B 3/13* (2006.01)
(Continued)

(52) U.S. Cl.
CPC ............... *H04N 23/73* (2023.01); *A61B 3/13* (2013.01); *G06T 3/40* (2013.01); *G06T 7/13* (2017.01);
(Continued)

(58) Field of Classification Search
CPC ........ H04N 23/73; H04N 23/74; H04N 23/71; A61B 3/13; A61B 3/135; G06T 3/40; G06T 7/13; G06T 2207/10056; G06V 10/60
See application file for complete search history.

(56) References Cited

U.S. PATENT DOCUMENTS

| | | |
|---|---|---|
| 5,382,988 A | 1/1995 | Nanjo |
| 5,387,952 A | 2/1995 | Byer |
| (Continued) | | |

FOREIGN PATENT DOCUMENTS

| | | |
|---|---|---|
| DE | 101 38 158 | 2/2003 |
| EP | 3 260 040 | 12/2017 |
| (Continued) | | |

OTHER PUBLICATIONS

Int'l Search Report (Form PCT/ISA/210) conducted in Int'l Application No. PCT/EP2021/051481 (Sep. 28, 2021).
(Continued)

*Primary Examiner* — Howard D Brown, Jr.
(74) *Attorney, Agent, or Firm* — GREENBLUM & BERNSTEIN, P.L.C.

(57) ABSTRACT

Image exposure in an ophthalmic microscope device is controlled by first recording a camera image with the camera of the microscope using first exposure parameters. Edge detection, e.g., based on convolution using a discrete differential operator, is then used to identify regions where the image has high and low edge densities. A brightness parameter of the camera image is calculated by weighing the pixel brightness in the regions with increased edge density more strongly than in the other regions. The brightness parameter is then used to control the exposure parameters of the microscope.

11 Claims, 3 Drawing Sheets

(51) Int. Cl.
  *G06T 3/40* (2006.01)
  *G06T 7/13* (2017.01)
  *G06V 10/60* (2022.01)
  *H04N 23/73* (2023.01)
  *H04N 23/74* (2023.01)
(52) U.S. Cl.
  CPC ............ *G06V 10/60* (2022.01); *H04N 23/74* (2023.01); *G06T 2207/10056* (2013.01)

(56) References Cited

U.S. PATENT DOCUMENTS

| | | | |
|---|---|---|---|
| 7,338,172 | B2 | 3/2008 | Yoshimura et al. |
| 7,515,321 | B2 | 4/2009 | Mimura et al. |
| 7,819,528 | B1 | 10/2010 | Dudee |
| 2013/0110091 | A1* | 5/2013 | Berry ..................... A61F 9/008 606/5 |
| 2016/0166142 | A1 | 6/2016 | Kobayashi |
| 2016/0278635 | A1* | 9/2016 | Fukuma ............... A61B 3/0025 |
| 2016/0278636 | A1* | 9/2016 | Fukuma ................ A61B 3/132 |
| 2019/0282091 | A1 | 9/2019 | Matsunobu |
| 2019/0328225 | A1* | 10/2019 | Enoki .................... G02B 21/06 |
| 2021/0015362 | A1 | 1/2021 | Soma et al. |
| 2022/0192489 | A1* | 6/2022 | Durant .................... A61B 3/14 |
| 2023/0181025 | A1* | 6/2023 | Hallen ................. A61F 9/0079 600/249 |

FOREIGN PATENT DOCUMENTS

| | | |
|---|---|---|
| EP | 3 530 228 | 8/2019 |
| EP | 3 644 044 | 4/2020 |
| JP | 2010-131332 | 6/2010 |
| JP | 2015-029865 | 2/2015 |
| TW | 201 212 641 | 3/2012 |
| WO | 2018/105411 | 6/2018 |
| WO | 2019/181554 | 4/2021 |

OTHER PUBLICATIONS

Int'l Written Opinion (Form PCT/ISA/237) conducted in Int'l Application No. PCT/EP2021/051481 (Sep. 28, 2021).
Kaur et al., "Improved Color Edge Detection . . . ", Int'l Journal of Science, Engineering and Technologies (IJSET), vol. 2, No. 1, pp. 1- 8 (2015).
Wikipedia—Discrete Laplace operator (7 pages).
Wikipedia—Edge detection (10 pages).
Laplacian/Laplacian of Gaussian, from https://homepages.inf.ed.ac.uk/rbf/HIPR2/log.htm (7 pages).
Japan Office Action conducted in counterpart Japan Appln. No.2023-544398 (Jul. 23, 2024).

* cited by examiner

IMAGE EXPOSURE TECHNIQUES FOR OPHTHALMIC MICROSCOPE DEVICES

TECHNICAL FIELD

In invention relates to a method for controlling image exposure in an ophthalmic microscope device as well as to an ophthalmic microscope device with a control unit adapted to execute this method.

BACKGROUND ART

Ophthalmic microscope devices, such as slit lamp microscopes or fundus cameras, have an illumination source, such as a slit lamp, for illuminating the subject's eye as well as a microscope for viewing it. Often, the microscope includes a camera.

When recording images with the camera, the exposure time, aperture width, gain, and/or illumination time may be adjusted automatically to implement exposure correction. For example, the average brightness value of the recorded image may be calculated, and the exposure parameters may then be changed to adjust this average brightness value to a desired value.

DISCLOSURE OF THE INVENTION

The problem to be solved by the present invention is to provide a method and a microscope of the type mentioned above that provide improved image quality.

This problem is solved by the method and microscope of the independent claims.

Accordingly, the method for controlling image exposure in an ophthalmic microscope device having a camera and an illumination source comprises at least the following steps:

Recording a camera image with the camera using first exposure parameters: The "camera image" may be the original image as recorded by the camera itself or an image derived therefrom, e.g. by changing the resolution and/or compression and/or by applying first image processing steps.

Using edge detection to identify at least one first sub-region and at least one second sub-region of the camera image (M, wherein the first sub-region has higher edge density than the second sub-region. The sub-regions may e.g. correspond to certain subsets of the (possibly downscaled) pixels of the camera image.

Calculating a brightness parameter of the camera image by weighing the pixel brightness in the first sub-region more strongly than the pixel-brightness in the second sub-region. In other words, if pixel A of the camera image is a pixel in the first sub-region and a pixel B of the camera image is a pixel in the second sub-region, the brightness of pixel A will affect the brightness parameter more strongly than the brightness of pixel B. For example, the brightness of pixel B may be ignored completely or be scaled down to have a weaker influence on the brightness parameter.

Depending on the brightness parameter, the first exposure parameters are adjusted to obtain second exposure parameters: For example, if the brightness parameter is too low, exposure time, illumination strength, aperture diameter, and/or camera gain may be increased. At least one of the parameters may be adjusted or several of them.

Using the second exposure parameters, an adjusted image is recorded with the camera.

This method is based on the understanding that, in ophthalmologic microscopy, the depth of field is small and typically will only cover the region of interest or a part thereof. A substantial part of the scene is typically out-of-focus and will not exhibit sharp pixel intensity changes in the corresponding image areas.

Hence, by weighting edge-rich sub-regions of the camera image more strongly than more uniform sub-regions for calculating the brightness parameter, a better exposure can be achieved for the sub-region(s) of interest. This may result in more "homogeneous" parts of the image being underexposed or overexposed, but these parts are typically not of interest.

The steps of the method are advantageously carried out automatically, e.g. by the control unit of the microscope.

The step of determining the first and second sub-regions may include the step of computing an edge intensity image having pixel values that are indicative of the presence of edges at the respective pixels.

Such an edge intensity image may e.g. be calculated using a discrete convolutional operator, such as a Sobel or Laplace filter. The operation may be carried out e.g. on the camera image or on an image derived therefrom, such as on a grayscale version of the camera image and/or a scaled-down version of the camera image. The edge intensity image may then be spatially averaged by e.g. spatial smoothing or down-scaling to obtain an image that reflects both intensity and density of edges.

In the step of determining the first and second sub-regions, different weights may be assigned to different predetermined parts of the image. For example, parts of the image closer to its center may be weighed more strongly than parts further away from the center. Then, the edge density is weighed with the different weights before identifying the first sub-region and the second sub-region. In other words, the different parts will gain different importance. For example, by weighing the center of the image more strongly, the calculated brightness parameter becomes more sensitive to edge structures in the center of the image.

The present method allows to concentrate the exposure control on parts of the image that are in focus, namely on the parts that have a high density of edges. Other areas, which may be much larger but that are more or less uniform, are weighed less strongly or not at all when calculating the brightness parameter. This is in contrast to conventional exposure control methods, where a large, uniform area may dominate the exposure parameters.

The invention also relates to an ophthalmic microscope device, in particular a slit lamp, which has an illumination source, a camera, and a control unit. The control unit is connected to the illumination source and the camera, and it is adapted (e.g. by programming and/or hardware) to execute the method of the present invention.

BRIEF DESCRIPTION OF THE DRAWINGS

The invention will be better understood and objects other than those set forth above will become apparent when consideration is given to the following detailed description thereof. Such description makes reference to the annexed drawings, wherein:

Note: FIGS. 4 and 5 are dithered for print. The actual images are e.g. true scalar images.

MODES FOR CARRYING OUT THE INVENTION

Definitions

"Multiplying" two pixel-based images is understood as multiplying each pixel value of the first image with the corresponding pixel value of the second image to calculate the respective pixel value of the resulting image. Optionally, the images may be rescaled before such an operation such that each pixel of the first image is assigned to a defined pixel of the second image or vice versa.

If one of the images has multi-component pixel values (e.g. RGB-values) and the second one has scalar pixel-values, the multiplication may e.g. consist of multiplying each multi-component pixel value of the first image with the pixel value of the second image, resulting in an image that again has multi-component pixel values. In another variant, the multiplication may first combine the multi-component pixel values of a pixel of the first image into a single value, e.g. using an averaging operation, and subsequent multiplication of the single value with the pixel value of the second image, in which case the resulting image has scalar pixel-values.

The term "edge density" is any measure that correlates with the number and magnitude of discontinuities in pixel intensity in a given sub-region of the image. It may e.g. be the value of the discrete Laplace transform as described below, the power of the 2D Fourier spectrum above a given frequency, etc.

Hardware

Figure 1:
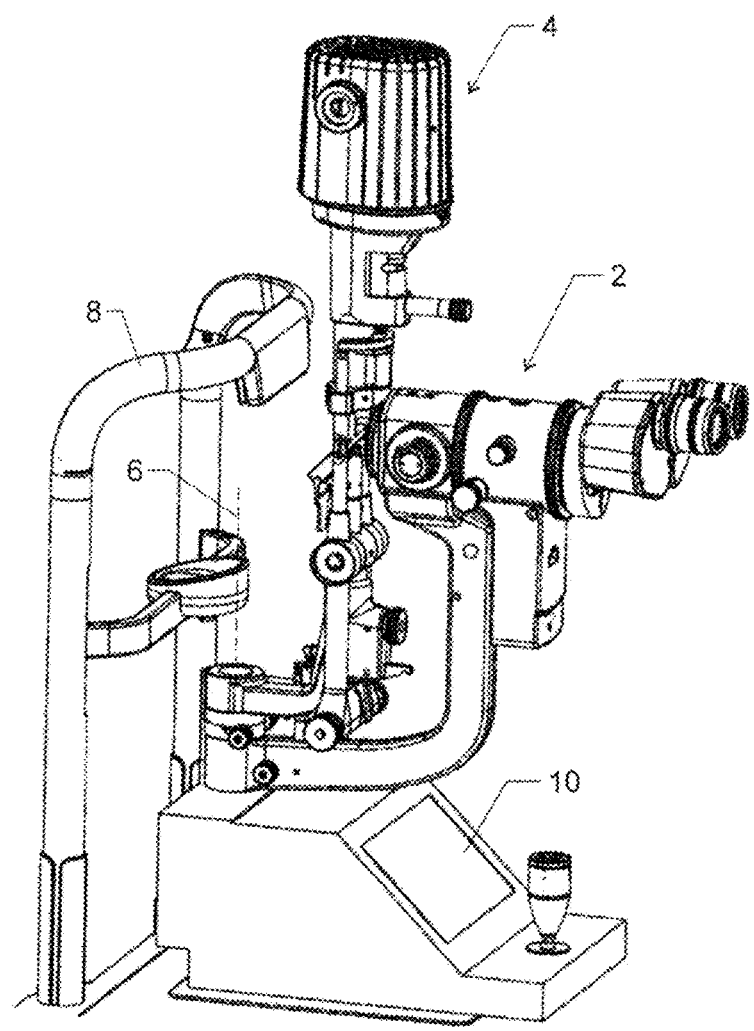
FIG. 1 is a view of a slit lamp microscope.

FIG. 1 shows a slit lamp microscope as an example for an ophthalmic microscope device. The device comprises a microscope 2 and an illumination source 4, such as a slit lamp. Both these elements can e.g. be pivoted about a common pivot axis 6 and be used to view a subject's eye.

A headrest 8 may be provided for the subject to rest his/her head on.

The device further may have an external display 10, which is advantageously a touch screen.

The user of the microscope device may view the image of the subject's eye either on display 10 or, directly, by using an eyepiece 12 of microscope 2.

Figure 2:
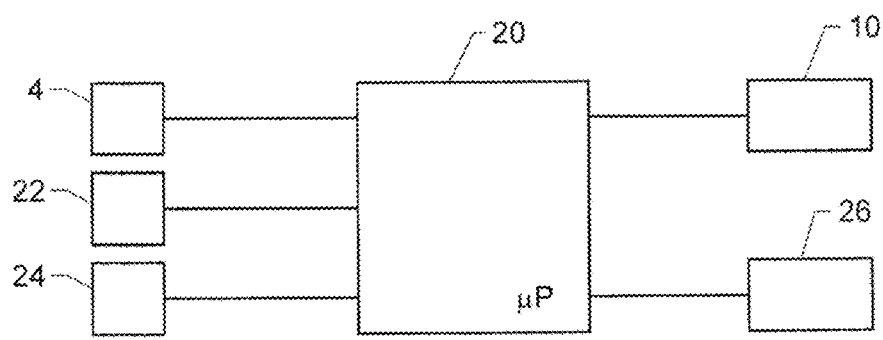
FIG. 2 is a functional block circuit diagram of the microscope.

FIG. 2 shows a functional block circuit diagram of the microscope device. The device comprises a control unit 20, which is e.g. a microprocessor equipped with suitable memory and programmed to provide the functionality of the device. Control unit 20 may be built into the device itself or be an external part of the device.

Control unit 20 is connected to illumination source 4, to an electronic camera 22 of microscope 2, and to further parts 24 of the device, such as to an adjustable aperture in the imaging optics of microscope 2.

Control unit 20 may also be connected to external display 10 and/or to an internal display 26 (see below).

Figure 3:
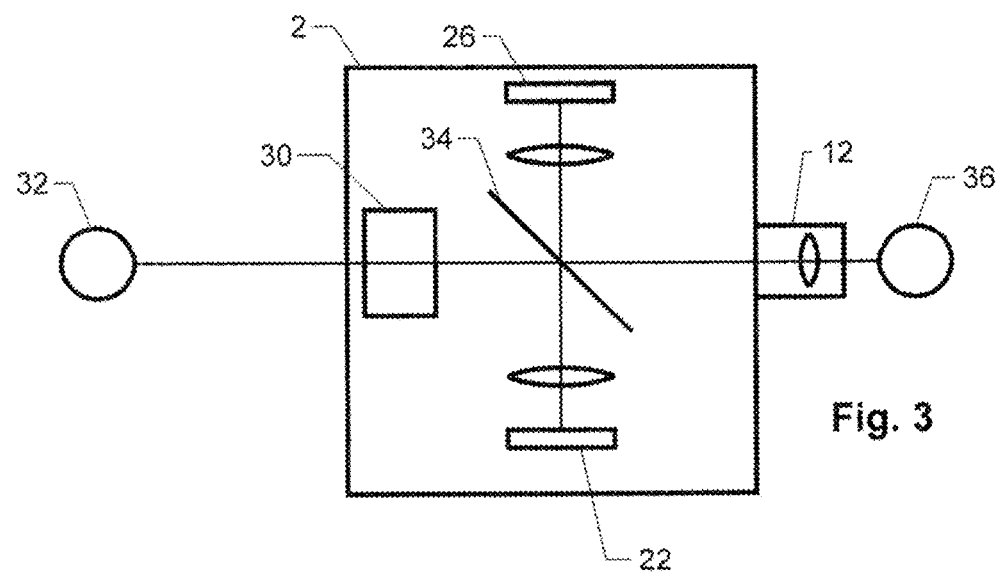
FIG. 3 is a schematic drawing of part of the optics of the microscope.

FIG. 3 shows a schematic drawing of the optics of microscope 2. It comprises objective optics 30 for taking an image of the subject's eye 32. Objective optics 30 may have a variable magnification and/or an adjustable aperture controlled by control unit 20.

The light from objective optics 30 is sent through a beam splitter 34, where part of it is transmitted to eyepiece 12 to be directly viewed by the user 36.

Beam splitter 34 reflects part of the light from objective optics 30 to camera 22, which may e.g. be a CCD camera.

In addition, microscope device 2 may comprise the internal display 26 mentioned above. The light from internal display 26 is sent to beam splitter 34, where part of it is reflected into eyepiece 12, which allows the user to view the information displayed on internal display 26.

Exposure Control

Control unit 20 is adapted and programmed to automatically select suitable exposure parameters when recording an image with camera 22. These parameters may be one or more of the following:

The brightness of illumination source 2: This brightness may be adjusted e.g. by adjusting the electrical current through illumination source 2.

The pulse length of illumination source 2: Illumination source 2 may be operated in pulsed mode while recording an image, i.e. it may emit one or more light pulses while recording a single frame by means of camera 22. In that case, the total duration of the light pulse(s) while recording the fame can be adjusted to obtain a suitable exposure.

The aperture diameter of the microscope: If microscope 2 comprises an adjustable aperture as mentioned above, the diameter of the aperture may be changed by control unit 20 for reducing or increasing exposure.

The gain of the camera.

The sampling time of the camera, i.e. the integration time while taking a single image.

To find the suitable exposure parameter(s), control unit 20 first takes a "camera image" with camera 22. From this camera image, it calculates a brightness parameter B as described below. If the brightness parameter B indicates that the image is not bright enough, control unit 20 increases one or more of the exposure parameters mentioned above and then takes an "adjusted image" by means of camera 22.

In particular, control unit 20 may implement a control loop where it tries to adjust the brightness parameter B of several consecutive images taken by camera 22 to a desired value by changing the one or more exposure parameters.

Calculating the Brightness Parameter

The present method is based on measuring at least one brightness parameter B from an image recorded by the camera. In the following, steps to calculate this parameter are described in more detail.

Step 1: Recording the Camera Image

In a first step, the camera image M is recorded by means of camera 22. The camera image is a pixel-based representation of the image recorded by the camera. This may e.g. be a color image, a gray-scale image, or a false-color image. As mentioned above, it can be the raw image taken by camera 22 or be derived from this raw image by first image processing steps.

Step 2: Calculating a Grayscale Image

In a next step, a grayscale image G may be calculated from camera image M, i.e. an image where each pixel $G_{ij}$ (with i=1 . . . N and j=1 . . . M) is a scalar value indicative of the "brightness" at the given pixel area. If camera image M is a color image, gray scale image G may e.g. be calculated from a weighted average of the RGB-values of camera image M.

Step 3: Computing an Edge Intensity Image

In a next step, an edge intensity image E is calculated, e.g. from grayscale image G (if the grayscale image has been calculated) or from camera image M directly. The pixel values $E_{ij}$ of edge intensity image E are indicative of the presence of discontinuities between $G_{ij}$ and its neighboring pixels.

For example, edge intensity image E can be calculated from gray-scale image G using the 2D discrete Laplace operator D in a convolution operation and taking the absolute values of the result, i.e.

$$E_{ij}=|(D*G)_{ij}|. \quad (1)$$

The discrete Laplace operator D is e.g. calculated using a convolution with a suitable kernel, with the kernel calculating weighted differences between the values of a pixel and its neighboring pixels, see e.g. https://en.wikipedia.org/wiki/Discrete_Laplace_operator. The Laplacian is a 2D isotropic measure of the 2nd spatial derivative of an image. It highlights regions of rapid intensity change.

Instead of using the absolute discrete Laplace operator D, other edge sensitive filters such as Prewitt, Roberts, Sobel, Scharr, etc. might be used instead. Scharr is presently preferred. Also the edge intensity image may be spatially averaged e.g. by down-scaling to obtain a filtered image that reflects both, intensity and density of edges.

Note that the edge intensity image may also be computed from the camera image M directly, which e.g. allows to detect edges in hue or saturation that may not be apparent in grayscale space.

Instead of calculating a complete edge intensity image, edge detection can be used, generally, to identify at least one region of the camera image that has a high edge density and another region that has a low edge density, e.g. by dividing the camera image into several sub-regions, calculating the Fourier transform of each sub-region, and identifying the one that has a the strongest high-frequency spectral components.

Step 4: Offsetting the Edge Intensity Image

In optional Step 4, the edge intensity image is offset by some fixed value $$E'=E+\text{off} \quad (2)$$

This causes areas with a low density/intensity of edges to still have a minimal effect on the final exposure.

Step 5: Add Vignetting

In an optional Step 5, the edge intensity image E (or E') is multiplied, pixel-wise, with a filter image F that has higher values in the center of the image than at the edges of the image. The result of this step is a weight image W:

$$W_{ij}=E'_{ij} \cdot F_{ij} \quad (4)$$

Filter image F may e.g. be a Gaussian distribution of values centered on the image, e.g.

$$F_{ij} \propto \exp\left(-\left(\frac{i-\frac{N}{2}}{k \cdot N}\right)^2 - \left(\frac{j-\frac{M}{2}}{k \cdot M}\right)^2\right) \quad (5)$$

with a shape variable k>0.

Alternatively, filter image F can be any other pixel distribution that favors certain predefined parts of the image while reducing the importance others. Advantageously, it has highest pixel values $F_{ij}$ in the center of the image and the pixel values decrease monotonously with increasing distance from the center of the image.

Step 6: Normalize

The result of the previous steps, the weight image W may be normalized (unless normalization is carried out in another step of the method), i.e. its pixel values are scaled such that their sum equals a given, predefined value (i.e. a value independent of the camera image), in particular 1. For example, the normalized weight image W' can be calculated as $$W'_{ij} = \frac{W_{ij}}{\Sigma_{i,j} W_{ij}}. \quad (6)$$

Step 7: Calculate the Brightness Parameter

Using the normalized weight image W', the brightness parameter B can be calculated as a weighted sum of all pixels of grayscale image G, with the weights given by the weight image:

$$B=\Sigma_{i,j} W'_{ij} \cdot G_{ij} \quad (7)$$

Brightness parameter B is a weighted sum of the brightness of the pixels of grayscale image G, with the weight being higher for the pixels at edge structures and (if vignetting was used) for the pixels closer to e.g. the center of the image.

Instead of calculating the brightness parameter B from grayscale image G, it may also be calculated e.g. from a multiplication with camera image M directly, again by weighing its pixel values with the pixel values of the weight image W.

Image Resolution

In the above example for calculating the brightness value, it was assumed that all images have the same resolution.

It must be noted, though, that the resolution of the various images may vary. Mapping operations may be used between the individual steps and/or when mathematically combining individual images.

For example, the resolution of camera image M is not necessarily the same as the resolution of the camera. For example, a part of the image recorded by the camera may e.g. have been cut off (e.g. when only a square region of a rectangular, non-square camera is used), and/or the resolution of the image of the camera may have been downscaled to derive camera image M for faster processing.

Similarly, edge intensity image E may be downscaled before offsetting, vignetting, normalizing, and/or calculating the brightness parameter. This can be seen as a way of spatial averaging turning the edge intensity into a combined edge intensity/density information. The advantages of such downscaling are two-fold. On the one hand, processing becomes faster. On the other hand, the pixels close to an edge structure in the camera image M will be given larger weight even if they are not right at an edge structure.

Example

Figure 4:
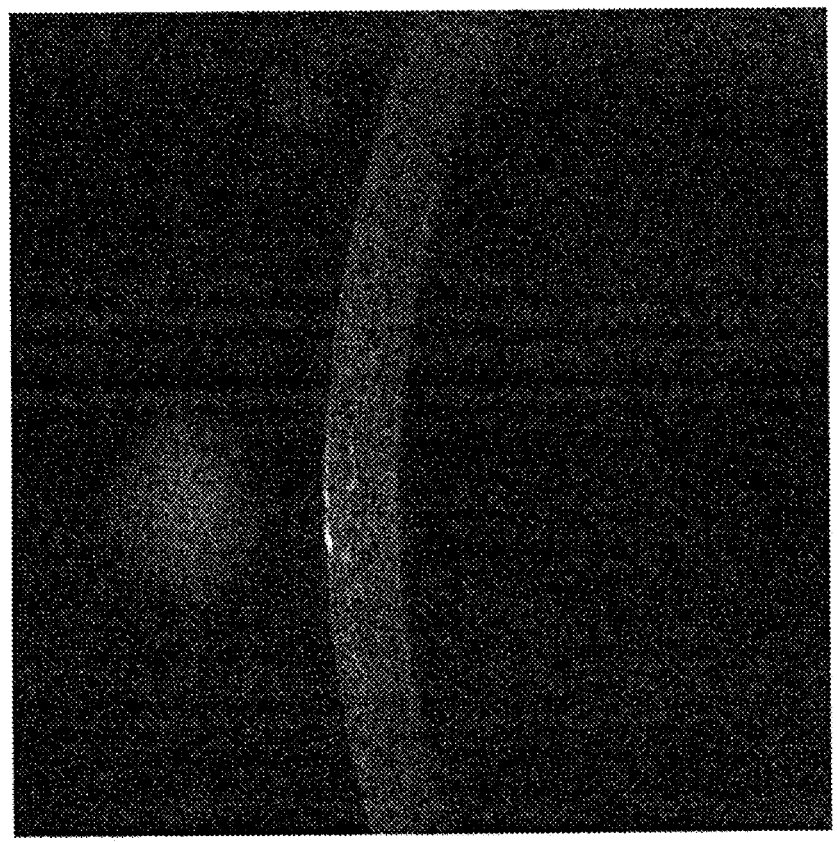
FIG. 4 is a grayscale version of an image recorded by the camera.

FIG. 4 shows a (dithered) grayscale image G as taken by a slit-lamp microscope. The image shows an edge-rich region corresponding to a section of cornea highlighted by a slit illumination.

Figure 5:
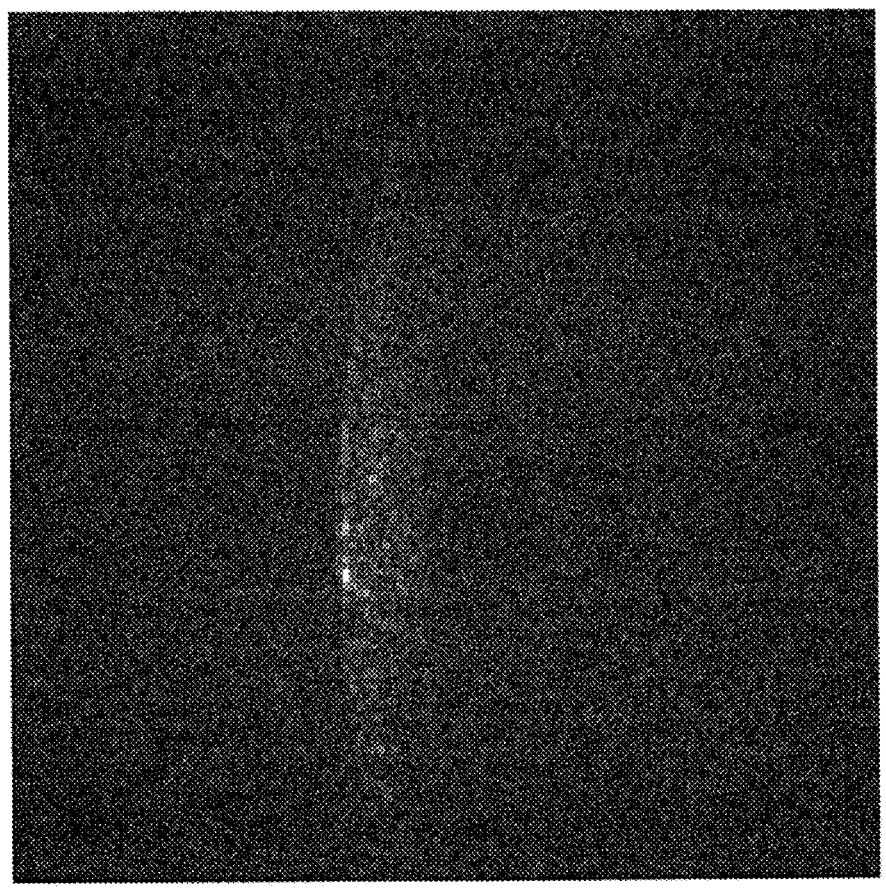
FIG. 5 represents the weight image as calculated by the method.

FIG. 5 shows weight image W as calculated from the grayscale image of FIG. 4 using the steps above. As can be seen, it has high (bright) values in the center within the edge-rich structures of FIG. 4.

Notes

In above Steps 3 to 5, edge detection is used to identify at least one "first sub-region" of the camera image that has a high edge density. This first sub-region may e.g. correspond to the pixels of edge intensity image E or E' having high values or, if edge detection based on a 2D Fourier-transform is used, to the sub-region(s) having strongest high-frequency spectral components. Similarly, at least one "second sub-region" is identified that has low edge density. This second sub-region may e.g. correspond to the pixels of edge intensity image E or E' having low values or, if edge detection based on a 2D Fourier-transform is used, to the sub-region(s) having the lowest high-frequency spectral components The identification process for the first and second sub-regions may, as in step 5, use a second set of weights that are assigned to predetermined parts of the image and multiplied with the weights from step 4. In this context, "predetermined parts" are parts whose location is independent of the contents of the camera image M.

In the example above, the pixels of filter image F are indicative of these predetermined parts in that they have high values in parts that are to be weighed more strongly. When calculating Eq. (4), the edge density as embodied by edge density image E or E' is weighed with the different weights of the predetermined parts of the image, with the weights being embodied by filter image F. In the specific example, parts closer to a center of the image are weighed more strongly than parts further away from the center.

In particular, the identification process for the first and second sub-regions may favor, as the first sub-region, sub-regions close to the center of the image. In other words, parts closer to the center of the image are weighed more strongly than parts further away from the center.

Steps 6 and 7 then calculate the brightness parameter B of the camera image by weighing the pixel brightness in the first sub-region more strongly than the pixel-brightness in the second sub-region. In the example, it calculates the average of the weighted sum of the pixels of the grayscale image.

In a more general embodiment, Eq. (7) may be replaced by $$B = f_1(\Sigma_{i,j} f_2(W_{ij} \cdot G_{ij})), \quad (7)$$

wherein $f_1$ and $f_2$ are monotonous functions. In other words, the brightness parameter may depend non-linearly on the product $W_{ij} \cdot G_{ij}$.

While there are shown and described presently preferred embodiments of the invention, it is to be distinctly understood that the invention is not limited thereto but may be otherwise variously embodied and practiced within the scope of the following claims.

The invention claimed is:

1. A method for controlling image exposure in an ophthalmic microscope device, wherein the ophthalmic microscope device has a camera and an illumination source, and wherein the method comprises:
   recording a camera image with the camera using first exposure parameters,
   using edge detection to identify at least one first sub-region and at least one second sub-region of the camera image, wherein the first sub-region has a higher edge density than the second sub-region,
   calculating a brightness parameter of the camera image by weighing pixel brightness in the first sub-region more strongly than pixel-brightness in the second sub-region,
   depending on the brightness parameter, adjusting the first exposure parameters to obtain second exposure parameters, and
   recording an adjusted image with the camera using the second exposure parameters.

2. The method of claim 1, wherein the determining the first and second sub-regions includes computing an edge intensity image (E, E') having pixel values indicative of the presence of discontinuities at their respective pixels.

3. The method of claim 2, wherein the edge intensity image (E, E') is calculated applying a discrete convolutional operator on the camera image or on an image derived from the camera image.

4. The method of claim 1, wherein, in the identifying the first and second sub-regions, different weights are assigned to different predetermined parts of the image, wherein the edge density is weighed with the different weights before identifying the first sub-region and the second sub-region, and in particular wherein parts closer to a center of the image are weighed more strongly than parts further away from the center.

5. The method of claim 4, wherein the determining of the first and second sub-regions includes computing an edge intensity image (E, E') having pixel values indicative of the presence of discontinuities at their respective pixels, and
   the method further comprising calculating a weight image (W, W') by multiplying the edge intensity image (E, E') with a filter image, wherein the filter image has pixel values indicative of the predetermined parts of the image.

6. The method of claim 5, further comprising the step of multiplying the weight image (W, W') with the camera image or with an image derived from the camera image, in particular with a grayscale image of the camera image.

7. The method of claim 6, wherein,
   prior to multiplying the weight image (W, W') with the camera image, the weight image is normalized by scaling it such that a sum of its pixel values equals a given, predefined value,
   and then calculating the brightness parameter B from
   $$B = f_1(\Sigma_{i,j} f_2(W_{ij} \cdot G_{ij}))$$
   wherein $f_1$ and $f_2$ are monotonous functions.

8. The method of claim 1, further comprising calculating a grayscale image of the camera image, wherein the first and second sub-regions are identified using the grayscale image.

9. The method of claim 1, further comprising adjusting, depending on the brightness parameter, at least one of the following parameters:
   a brightness of the illumination source,
   a pulse length of the illumination source,
   an aperture diameter of the microscope,
   a gain of the camera, and
   a sampling time of the camera.

10. An ophthalmic microscope device comprising:
    an illumination source,
    a camera, and
    a control unit connected to the illumination source and the camera, wherein said control unit is adapted to execute the method of claim 1.

11. The method of claim 4, wherein parts closer to a center of the image are weighed more strongly than parts further away from the center.

* * * * *